United States Patent [19]

Chandraratna

[11] Patent Number: 5,696,162
[45] Date of Patent: Dec. 9, 1997

[54] PHENYL OR HETEROARYL AND TETRAHYDRONAPHTHYL SUBSTITUTED DIENE COMPOUND HAVING RETINOID LIKE BIOLOGICAL ACTIVITY

[75] Inventor: Roshantha A. Chandraratna, Missio Viejo, Calif.

[73] Assignee: Allergan, Waco, Tex.

[21] Appl. No.: 460,487

[22] Filed: Jun. 2, 1995

Related U.S. Application Data

[62] Division of Ser. No. 138,275, Oct. 18, 1993, Pat. No. 5,475,022.

[51] Int. Cl.⁶ .......................... A61K 31/325; A61K 31/19; C07C 69/76; C07C 63/69
[52] U.S. Cl. .......................... 514/532; 514/534; 514/569; 514/617; 514/730; 560/100; 562/490; 564/617; 568/808
[58] Field of Search ............... 560/8, 9, 100, 560/37.51; 562/405, 490, 467; 564/180, 171, 428; 568/808; 514/532, 534, 569, 617, 730

[56] References Cited

U.S. PATENT DOCUMENTS

| 4,096,341 | 6/1978 | Frazer .................... 560/85 |
| 4,326,055 | 4/1982 | Loeliger ................. 542/429 |
| 4,391,731 | 7/1983 | Boller et al. ........... 252/299.62 |
| 4,439,614 | 3/1984 | Dawson et al. ........... 560/8 |
| 4,454,341 | 6/1984 | Dawson et al. ......... 560/100 |
| 4,456,618 | 6/1984 | Dawson et al. ......... 424/308 |
| 4,532,343 | 7/1985 | Dawson et al. ......... 514/543 |
| 4,578,498 | 3/1986 | Frickel et al. ............ 560/8 |
| 4,695,649 | 9/1987 | Magami et al. .......... 560/86 |
| 4,722,939 | 2/1988 | Loev et al. .............. 514/529 |
| 4,723,028 | 2/1988 | Shudo ..................... 560/8 |
| 4,739,098 | 4/1988 | Chandraratna ............ 560/8 |

(List continued on next page.)

FOREIGN PATENT DOCUMENTS

| 0098591 | 1/1984 | European Pat. Off. . |
| 0130795 | 1/1985 | European Pat. Off. . |
| 0176032 | 4/1986 | European Pat. Off. . |
| 0176033 | 4/1986 | European Pat. Off. . |
| 176034A | 4/1986 | European Pat. Off. . |
| 0253302 | 1/1988 | European Pat. Off. . |
| 0272921 | 6/1988 | European Pat. Off. ...... C07D 213/80 |
| 0284288 | 9/1988 | European Pat. Off. . |
| 0303915 | 2/1989 | European Pat. Off. . |
| 0315071 | 5/1989 | European Pat. Off. . |
| 0350846 | 7/1989 | European Pat. Off. . |
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2164938 | 4/1986 | United Kingdom . |
| 2190378 | 11/1987 | United Kingdom . |
| 8500806 | 2/1985 | WIPO . |
| 8504652 | 10/1985 | WIPO . |
| WO9116051 | 10/1991 | WIPO . |
| WO9206948 | 4/1992 | WIPO . |

OTHER PUBLICATIONS

Mohanraj, Subramaniam, "Semi-Preparative HPLC separations of E and Z isomers of new aromatic retinoids", CA 101:171552 (1984).

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King; and William L. Klima, *J. Org. Chem.* 45 No. 12, 1980 p. 2526.

Sporn et. al. in *J. Amer. Acad. Derm.* 15:756–764 (1986).

(List continued on next page.)

Primary Examiner—José G. Dees
Assistant Examiner—Deborah Lambkin
Attorney, Agent, or Firm—Gabor L. Szekeres; Robert J. Baran; Martin A. Voet

[57] ABSTRACT

Compounds of Formula 1

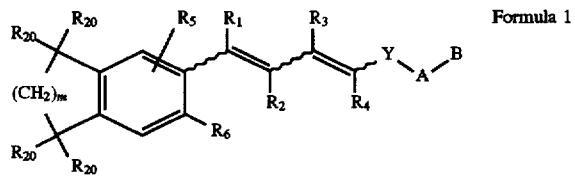

Formula 1 wherein m is 1–4; $R_1$–$R_4$ independently are hydrogen, lower alkyl of 1 to 6 carbons, Cl, Br, or I; $R_5$ is hydrogen, lower alkyl of 1 to 6 carbons, Cl, Br, I, lower alkoxy or lower thioalkoxy of 1–6 carbons; $R_6$ is hydrogen, lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$ OR $NR_{11}$—$COR_{11}$; $R_{20}$ is independently hydrogen or lower alkyl; Y is an aromatic group such as phenyl or naphthyl, or a heteroaryl group selected from a group consisting of pyridyl, thienyl, furyl, pyridazinyl, pyrimidinyl, pyrazinyl, thiazolyl and oxazolyl; A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower aklylphenyl, $R_{11}$ is lower alkyl, phenyl or lower alkylphenyl, $R_{12}$ is lower alkyl, and $R_{13}$ is divalent alkyl radical of 2–5 carbons, have retinoid like biological activity. In the compounds of the invention the A—B and the butadiene groups are attached to adjacent aromatic carbons of the Y moiety.

4 Claims, No Drawings

U.S. PATENT DOCUMENTS

| | | | |
|---|---|---|---|
| 4,740,519 | 4/1988 | Shroot et al. | 514/443 |
| 4,804,670 | 2/1989 | Waest et al. | 514/381 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,870,219 | 9/1989 | Klaus et al. | 570/189 |
| 4,895,868 | 1/1990 | Chandraratna | 514/432 |
| 4,927,947 | 5/1990 | Chandraratna | 549/484 |
| 4,929,635 | 5/1990 | Coquelet et al. | 514/438 |
| 4,980,369 | 12/1990 | Chandraratna | 514/432 |
| 4,992,468 | 2/1991 | Chandraratna | 514/456 |
| 4,994,491 | 2/1991 | Purcell et al. | 514/529 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 514/337 |
| 5,068,252 | 11/1991 | Chandraranta | 514/337 |
| 5,086,060 | 2/1992 | Haley et al. | 514/294 |
| 5,089,509 | 2/1992 | Chandraratna | 549/60 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraranta | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraranta | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraranta | 514/365 |
| 5,426,118 | 6/1995 | Chandraranta | 514/337 |
| 5,434,173 | 7/1995 | Chandraratna | 514/354 |

OTHER PUBLICATIONS

A Convenient Synthesis of Ethynylarenes and Diethynylarenes by S. Takagashi, Y. Kuroyama, K. Sonogashira, N. Hagihara, *Synthesis* 1980 pp. 627–630.

Shudo et al. in *Chem. Pharm. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, p.334–335, 354.

Synthesis of 2,2'–Diacyl–1,1'–biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3–g]isoquinoline Antipsychotics, Gary L. Olson, et al. *American Chemical Society*, 1981, vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., Journal of Cell *Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et.al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No.4, pp. 211–214, 1991.

Di–and Tri–methoxystyryl Derivatives of Heterocyclic Nitrogen Compounds by Bahner, C.T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989 , 32, pp. 1098–1108.

Chem Abastracts, vol. 101, No.19, 05.Nov.1984, Columbus, OH, abstract No.171552q, S. Mohanraj, "Semi–preparative HPLC separations of E and Z isomers of new aromatic retinoids", p.728 col. 2.

*Journal of Liquid Chromatography*, vol. 7, No. 7, 1984, pp. 1455–1460.

PHENYL OR HETEROARYL AND TETRAHYDRONAPHTHYL SUBSTITUTED DIENE COMPOUND HAVING RETINOID LIKE BIOLOGICAL ACTIVITY

CROSS-REFERENCE TO RELATED APPLICATION

The present application is a divisional of application Ser. No. 08/138,275 filed on Oct. 18, 1993 U.S. Pat. No. 5,475,022.

BACKGROUND OF THE INVENTION

1. Field of the Invention

The present invention is directed to novel compounds which have retinoid like biological activity. More specifically, the present invention relates to diene compounds substituted with a phenyl or heteroaromatic moiety where the ring connection is adjacent to a substituent group in the heterocycle, the diene being further substituted with a tetrahydronaphthyl or analogous group. The present invention also relates to pharmaceutical compositions comprising these compounds as the active ingredient and to methods of using the compounds and compositions.

2. Brief Description of the Background Art

The biological activity of retinoic acid is known and has been the subject of numerous literature references.

A relatively large number of retinoic acid analogs (retinoid like compounds) have been synthesized in the prior art, and are described in numerous patents and scientific publications. For example, U.S. Pat. No. 4,326,055 discloses ethene derivatives which have a substituted phenyl ring and a substituted indane or tetrahydronaphthalene group. The compounds are described as tumor inhibiting agents, and useful for treating dermatological conditions and rheumatic illnesses.

U.S. Pat. No. 4,723,028 discloses diphenylethene (stilbene) derivatives which have retinoic acid-like activity.

U.S. Pat. No. 4,740,519 discloses certain aromatic heterocycle derivatives which have retinoic acid-like activity.

Published European Patent Application 0130795 discloses ethene derivatives, where the ethene moiety is substituted by a substituted phenyl group and by a substituted chroman, thiochroman or quinoline group. The compounds are useful for inhibiting the degradation of cartilage in mammals.

European Patent Application 176034A (Published Apr. 2, 1986) discloses tetrahydronaphthalene compounds having an ethynylbenzoic group. U.S. Pat. No. 4,739,098 discloses compounds wherein three olefinic units from the acid-containing moiety of retinoic acid are replaced by an ethynylphenyl functionality. These compounds have retinoic acid-like biological activity.

Published German Patent Application DE 3529032 A1 discloses di-phenyl substituted butadiene compounds having retinoid-like activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene group is a substituted phenyl group, and the second substitutent is a substituted or unsubstituted 6-chromanyl, 6-thiochromanyl or 6-tetrahydroquinolinyl group. The compounds disclosed and claimed in U.S. Pat. No. 4,810,864 have retinoic acid-like biological activity.

The publication Cancer Research 44, 190–195, January 1984 Dawson et. al. discusses the relationship between binding affinities to cellular retinoic acid binding protein and the biological potency of a new series of retinoids. The synthesis of the latter compounds is disclosed in Dawson, Journal of Medicinal Chemistry, 1981, Vol. 24, No.5 591.

A publication titled "Aromatic Retinoic Acid Analogues Synthesis and Pharmacological Activity" by M. I. Dawson et al. Journal of Medicinal Chemistry 1981 Vo. 24 p 583–592 discusses structure activity relationships of certain synthetic retinoids and describes the synthesis of certain phenyl and cyclohexenyl substituted butadienes and hexatrienes as retinoid analogs.

A publication by L. W. Spruce et al. titled Novel Heteroarotinoids: Synthesis and Biological Activity Journal of Medicinal Chemistry 1991 Vol. 34, p. 430 describes certain thiochromanyl and cyclopropyl substituted butadienes as retinoid analogs.

The synthesis of 2-furancarboxylic acid, 5-(methylthio)-3-(4-phenyl-1,3-butadienyl)-,ethyl ester is disclosed in Tetrahedron, 45(23), 7631–40 (Eng) 1989.

Several co-pending applications and recently issued patents of the present inventor, which are assigned to the assignee of the present application, are directed to further compounds having retinoic acid-like acitivity.

SUMMARY OF THE INVENTION

The present invention covers compounds of Formula 1

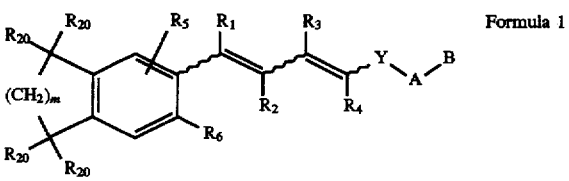

Formula 1 wherein m is 1–4;

$R_1$–$R_4$ independently are hydrogen, lower alkyl of 1 to 6 carbons, F, Cl, Br, or I;

$R_5$ is hydrogen, lower alkyl of 1 to 6 carbons, F, Cl, Br, I, lower alkoxy or lower thioalkoxy of 1–6 carbons;

$R_6$ is hydrogen, lower alkyl, F, Cl, Br, I, $OR_{11}$, $SR_{11}$, $OCOR_{11}$, $SCOR_{11}$, NH2, $NHR_{11}$, $N(R_{11})_2$, $NHCOR_{11}OR$ $NR_{11}$—$COR_{11}$;

$R_{20}$ is independently hydrogen or lower alkyl;

Y is an aromatic group such as phenyl or naphthyl, or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower aklylphenyl, $R_{11}$ is lower alkyl, phenyl or lower alkylphenyl, $R_{12}$ is lower alkyl, and $R_{13}$ is divalent alkyl radical of 2–5 carbons.

In the compounds of the invention the diene and A—B groups are attached to adjacent aromatic carbons such that for example in the compound where Y is phenyl, the phenyl moiety is ortho substituted.

In a second aspect, this invention relates to the use of the compounds of Formula 1 as regulators for cell proliferation and differentiation, and particularly as agents for treating dermatoses, such as ache, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointiural hyperproliferation, for treating and preventing other non-malignant hyperproliferative diseases such as endometrial hyperplasia, benign prostatic hypertrophy, proliferative vitreal retirropathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damge to skin.

The present invention also relates to a pharmaceutical formulation comprising a compound of Formula 1 in admixture with a pharmaceutically acceptable excipient.

The compounds of this invention of Formula 1 can be made by a process which comprises: reacting a compound of Formula 2 with a base and subsequently with a compound of Formula 3

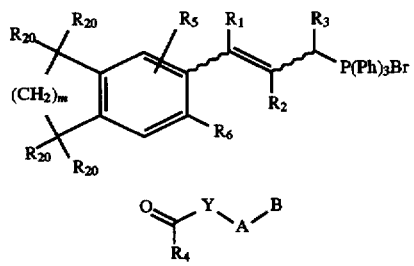

Formula 2

Formula 3 where the symbols are as described above in connection with Formula 1, except that for this reaction B is H, or a protected acid, alcohol, aldehyde or ketone. The A—B group on the Y ring is separated only by one aromatic bond from the $R_4$—CO moiety, giving the corresponding compound of Formula 1, or homologating a compound of Formula 1 where A is $(CH_2)_n$ and n is 0–4 to give an acid of Formula 1; converting an acid of Formula 1 to a salt; or forming an acid addition salt; converting an acid of Formula 1 to an ester; or converting an acid of Formula 1 to an amide; or reducing an acid of Formula 1 to an alcohol or aldehyde; or converting an alcohol of Formula 1 to an ether or ester; or oxidizing an alcohol of Formula 1 to an aldehyde; or converting an aldehyde of Formula 1 to an acetal; or converting a ketone of Formula 1 to a ketal.

GENERAL EMBODIMENTS

Definitions

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Where B (of Formula 1, is —COOH, this term covers the products derived from treatment of this function with alcohols, preferably with aliphatic alcohols having 1–6 carbons. Where the ester is derived from compounds where B is —CH$_2$OH, this term covers compounds of the formula —CH$_2$OOCR$_{11}$ where R$_{11}$ is any substituted or unsubstituted aliphatic, aromatic or aliphatic-aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound used in the method of treatment of this invention, if the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention which comprise novel composition of matter, contain at least two double bonds and therefore may have trans and cis (E and Z) isomers. In addition, some of the compounds used in the method of treatment of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

Methods of Administration

The compounds of this invention may be administered systemically or topically, depending on such considerations as the condition to be treated, need for site-specific treatment, quantity of drug to be administered, and similar considerations.

In the treatment of dermatoses particularly, topical administration may be used, though in certain cases such as treatment of severe cystic acne, oral administration may be preferred. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoid like compounds will be effected by administration of the therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

BIOLOGICAL ACTIVITY

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670, 1975 may be used to demonstrate inhibition of TPA induction of ODC by compounds of this invention. The results of this assay for certain examplary compounds of the invention are shown in Table 1 below.

TABLE 1

| Compound # | % ODC Inhibition at 1.0 μM concentration |
|---|---|
| 1 | 37 |
| 2 | 36 |
| 6 | 100* |
| 7 | 79 |
| 8 | 75 |
| 9 | 56 |
| 11 | 26 |
| 12 | 42 |
| 13 | 60 |
| 14 | 72 |
| 17 | 79 |
| 19 | 73 |
| 24 | 88 |

*value determined by linear regression of data collected at 30, 100, 300 nanomolar concentrations.

PREFERRED EMBODIMENTS

Referring now to the FORMULA 1 and with reference to the symbol m, the preferred compounds of the invention are 5,6,7,8-tetrahydronaphthalene derivatives wherein m is 2.

With reference to the symbol Y, the preferred compounds of the invention are those where Y is phenyl, furyl, or thienyl.

The substituent $R_1$ is preferably hydrogen or lower alkyl, more preferably lower alkyl, and most preferably methyl. The substituents $R_2$, $R_3$ and $R_4$ preferably are hydrogen or lower alkyl, more preferably H. The substitutent $R_5$ is preferably hydrogen or lower alkyl, more preferably hydrogen. The substituent $R_6$ is preferably hydrogen, lower alkyl, or halogen, more preferably H or methyl.

The substituents $R_{20}$ preferably are lower alkyl, more preferably methyl.

With regard to the side chain (substituent) on the phenyl or heteroaryl group Y, compounds are preferred where A is $(CH_2)_n$ and n is 0; and B is —COOH, and alkali metal salt or organic amine salt, or a lower alkyl ester thereof, or —$CH_2OH$ and the lower alkyl ester and ether thereof, (formed with a lower alkanol) or —CHO and acetal derivatives thereof.

The most preferred compounds of the present invention are shown in Table 2, with reference to Formula 4. In Formula 4 and elsewhere in this specification wavy lines connected to an ethylene moiety (double bonded carbons) indicate that the configuration about that double bond may be cis (Z) or trans (E). With particular reference to FIG. 4

(and elsewhere where it is applicable in the present description) the butadiene moiety is numbered such that the double bonded carbons more proximate to the tetrahydronaphthalene ring are carbons 4 and 3. Consequently, from "left to right" in the structural formula of FIG. 4 (and elsewhere where applicable) trans configuration of the first double bond is designated in the chemical name and in Table 2 as "3E", and trans configuration of the second double bond (left to right) is designated in the chemical name and in Table 2 as "1E". In Table 2 the Y substituent is described first by reference to the point of attachment of the respective aryl or heteroaryl moiety to carbon-1 of the butadiene moiety, and then the second position of substitution (in case of Formula 4 with the $COOR_8$ group) is designated. For example for Compound 1 the designation "2 furyl (3 substituted)" means that the 2 position of the furan ring is attached to the butadiene moiety and that the furan ring is substituted with an $R_8$ ($CH_3$) group in its 3 position. The compound number is a number assigned to certain compounds for ease of reference in the present description.

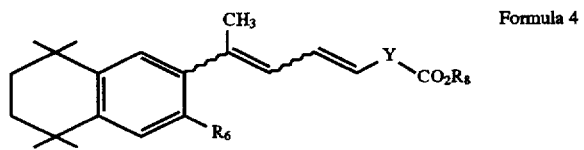

Formula 4

TABLE 2

| Compound No. | Stereo-chemistry at 3 | Stereo-chemistry at 1 | $R_6$ | Y | $R_8$ |
|---|---|---|---|---|---|
| 1 | 3E | 1E | $CH_3$ | 2-furyl (3-substituted) | $CH_3$ |
| 2 | 3Z | 1E | $CH_3$ | 2-furyl (3-substituted) | $CH_3$ |
| 3 | 3E | 1E | $CH_3$ | 1-phenyl (2-substituted) | $CH_2CH_3$ |
| 4 | 3Z | 1E | $CH_3$ | 1-phenyl (2-substituted) | $CH_2CH_3$ |
| 5 | 3Z | 1E | H | 1-phenyl (2-substituted) | $CH_3$ |
| 6 | 3E | 1E | H | 1-phenyl (2-substituted) | $CH_3$ |
| 7 | 3E | 1E | $CH_3$ | 1-phenyl (2-substituted) | H |
| 8 | 3Z | 1E | $CH_3$ | 1-phenyl (2-substituted) | H |
| 9 | 3Z | 1E | $CH_3$ | 2-furyl (3-substituted) | H |
| 10 | 3E | 1E | $CH_3$ | 2-furyl (3-substituted) | H |
| 11 | 3E | 1E | H | 2-furyl (3-substituted) | $CH_3$ |
| 12 | 3Z | 1E | H | 2-furyl (3-substituted) | $CH_3$ |
| 13 | 3E | 1E | H | 2-furyl (3-substituted) | H |
| 14 | 3Z | 1E | H | 2-furyl (3-substituted) | H |
| 15 | 3E | 1E | $CH_3$ | 3-thienyl (2-substituted) | $CH_2CH_3$ |
| 16 | 3Z | 1E | $CH_3$ | 3-thienyl (2-substituted) | $CH_2CH_3$ |
| 17 | 3E | 1E | $CH_3$ | 3-thienyl (2-substituted) | H |
| 18 | 3Z | 1E | $CH_3$ | 3-thienyl (2-substituted) | H |
| 19 | 3E | 1Z | $CH_3$ | 3-furyl (2-substituted) | $CH_2CH_3$ |
| 20 | 3E | 1Z | $CH_3$ | 2-thienyl (3-substituted) | $CH_3$ |
| 21 | 3E | 1E | $CH_3$ | 2-thienyl (3-substituted) | $CH_3$ |
| 22 | 3E | 1E | $CH_3$ | 2-thienyl (3-substituted) | H |
| 23 | 3E | 1Z | $CH_3$ | 2-thienyl (3-substituted) | H |
| 24 | 3E | 1E | $CH_3$ | 1-phenyl (2-substituted) | H |

Synthetic Processes for Preparing Compounds of the Invention

It is anticipated that the compounds of this invention can be made by a number of different synthetic chemical pathways. To illustrate this invention, there is here laid out a series of steps which will provide the compounds of Formula 1 where m is 2, (tetrahydronaphthalene derivatives) when such synthesis is followed in tone and in spirit. The synthetic chemist will readily appreciate that the conditions set out here are specific embodiments which can be generalized to any and all of the compounds represented by Formula 1. Specifically, in order to prepare the compounds of the invention where m is 1, 3, or 4 the sequence of reactions outlined in Reaction Scheme 1 is followed, but the sequence is started with a compound which is the indane, cycloheptanobenzene or cyclooctanobenze analog of Formula 5.

Reaction Scheme 1

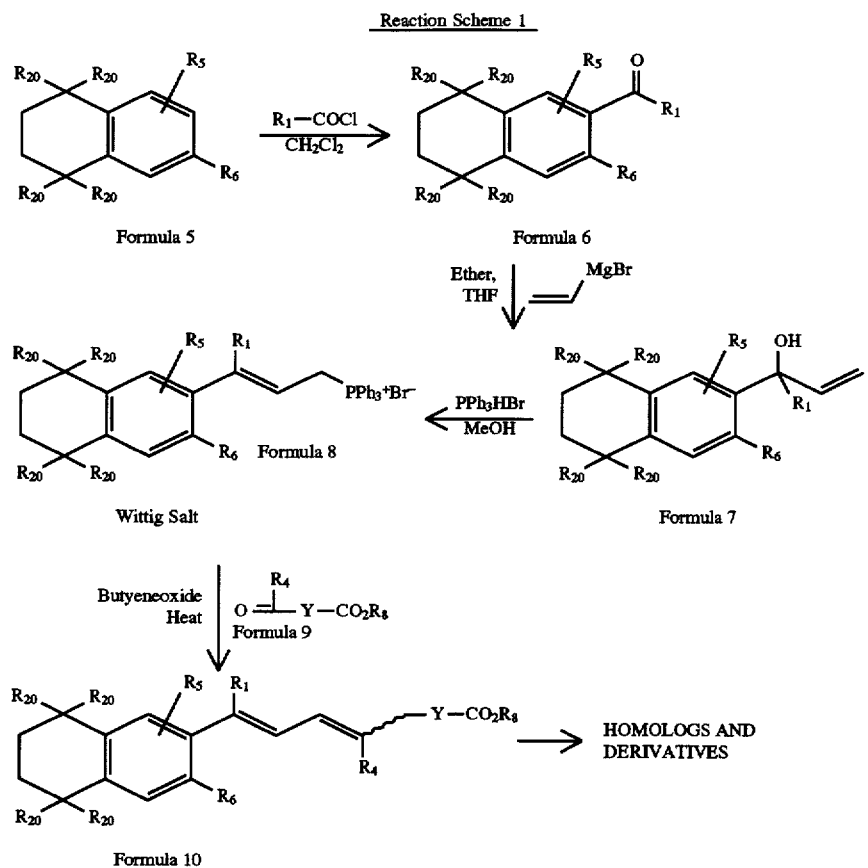

Formula 10

Reaction Scheme 1 shows a synthetic route to the compounds of the invention. A 5,5,7,8-tetrahydronapthalene compound of Formula 5, which has the desired $R_5$, $R_6$, and $R_{20}$ substitutents (as defined in connection with Formula 1) is reacted under Friedel Crafts like conditions with a reagent such as $R_1COCl$ ($R_1$ is defined in connection with Formula 1) to introduce the $R_1$—CO ketone function into the 2-position of the tetrahydronaphthalene nucleus. When $R_1$ is methyl then the reagent in the Friedel Crafts type reaction is typically acetyl chloride. The ketone of Formula 6 is reacted with vinyl magnesium bromide to give the tertiary alcohol of Formula 7. The alcohol of Formula 7 is reacted with triphenylphosphine hydrobromide. This reaction results in migration of the double bond and formation of the triphenylphosphonium salt of Formula 8 where the triphenylphosphonium moiety is attached to a primary carbon. The double bond obtained in this process is usually predominantly of trans (E) configuration. The triphenylphosphonium salt of Formula 8 is a Wittig reagent, which is reacted with the aromatic or heteroaromatic aldehyde or ketone of Formula 9 to provide the diene compound of Formula 10. In Formula 9 the symbols Y, $R_4$ and $R_8$ are defined as in connection with Formula 1, and also with the condition that the carbonyl ($R_4CO$—) and and carboxylic acid ester ($COOR_8$) substituents are attached to adjacent aromatic or heteroaromatic carbons (ortho substitution). The Wittig reaction is typically conducted in the presence of a base, such as 1,2-epoxybutane. The double bond formed in the Wittig reaction is a mixture of cis (Z) and trans (E) isomers, but the ratio of the trans (E) isomer can be increased by isomerization with iodine. The cis and trans isomers can usually be separated by appropriate techniques such as high pressure liquid chromatography (HPLC).

The Wittig reaction between the triphenylphosphonium salt of Formula 8 and the aldehyde or ketone of Formula 9 can also be conducted in the presence of n-BuLi or other appropriate bases.

The compound of Formula 10 which is formed as a result of the Wittig reaction has the essential structural features of the compounds used in accordance with the present invention. Thus, the compound of Formula 10 may be the target compound made in accordance with the invention, (in this case Formula 10 depicts compounds of Formula 1) or may be readily converted into the target compound by such steps as salt formation, esterification, deesterification, homologation, amide formation and the like. These steps are further discussed below.

Specifically, the compounds of Formula 10 may be subjected to further transformations, particularly as far as synthetic transformation of the $COOR_8$ group is concerned. As far as the synthesis of compounds analogous to the compounds of Formula 10, but differring therefrom in the functionality of the A—B group (see for example Formula 1) is concerned, (and by extension of the principles to any and all compounds of the invention) the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

A means for making compounds where A is $(CH_2)_n$ (n is 1-5) is to subject the compounds of Formula 1, (or of Formula 10) where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the aryl or heteroaryl intermediate which is coupled as an aldehyde or ketone with the triphenylphosphonium salt of Formula 8. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of Formula 1 where the A group has a triple (acetylenic) bond can be made by using the corresponding aryl or heteroaryl aldehyde or ketone intermediate. Such intermediate can be obtained by reactions well known in the art, for example, by reaction of a corresponding methyl ketone with strong base, such as lithium diisopropyl amide.

The acids and salts derived from compounds of Formula 1 and of Formula 10 are readily obtainable from the corresponding esters. Basic saponification with an alkali metal base will provide the acid. For example, an ester of Formula 1 or of Formula 10 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

With regard to the aryl or heteroaryl intermediate compounds of Formula 9, these are either available by procedures described in the chemical literature and therefore readily accessible to the practicing organic chemist, or can be readily prepared by adaptation of such literature procedures. Actual experimental processes for synthesizing several intermediates corresponding to Formula 9, such as 2-carboetoxy-3-furaldehyde, 3-carbomethoxy-2-thiophenecarboxaldehyde, 2-carbomethoxybenzaldehyde, 2-carboethoxy-3-thiophenecarboxaldehyde, are described below.

SPECIFIC EXAMPLES

1-[8,8-dimethyl (5,6,7,8-tetrahydronaphthalen)-2-yl] ethanol and 1-[8,8-dimethyl (5,6,7,8-tetrahydronaphthalen)-3-yl] ethanol To a stirred solution of 4.27 g (32.0 mmol) of anhydrous aluminum chloride in 15 ml of methylene chloride at 0° C. was added a solution of 4.0 g (25.0 mmol) of 1,1-dimethyltetralin (Davidson et al. J. Amer. Chem. Soc. 1934, 56 p 962) and 2.35 g (30.0 mmol) of acetyl chloride in 5 ml of methylene chloride. The mixture was allowed to warm to room temperature over a period of one hour and then treated with 70 ml of ice water. The organic layer was isolated and washed with 20 ml of dilute HCl, 40 ml of water, and 40 ml of brine and dried (MgSO4). Solvent was removed in-vacuo and the residue was purified using fractional distillation (97°–99° C., 0.1 mm). The resulting methyl [8,8-dimethyl (5,6,7,8-tetrahydronaphthalen)-2-yl] ketone and methyl [8,8-dimethyl (5,6,7,8-tetrahydronaphthalen)-3-yl] ketone isomers were separable only after reduction to the corresponding alcohols. To this end, lithium aluminum hydride (0.250 g, 6.7 mmol) in 30 ml of dry ether was added dropwise to a solution of 4.0 g (19.8 mmol) of methyl [8,8-dimethyl (5,6,7,8-tetrahydronaphthalen)-2-yl] ketone and methyl [8,8-dimethyl (5,6,7,8-tetrahydronaphthalen)-3-yl] ketone in 10 ml of anhydrous ether. The mixture was refluxed gently for 30 minutes and treated with ethyl acetate, water, and dilute hydrochloric acid. The organic layer was washed with water, brine and dried (MgSO4). Solvent was removed in-vacuo and the resulting isomeric mixture was purified and separated, using HPLC (Whatman M20 partisil, 10% ethyl acetate in hexanes at 9.9 ml per minute) to give the title compounds as colorless oils: 1-[8,8-dimethyl (5,6,7,8-tetrahydronaphthalen)-2-yl] ethanol, PMR(CDCl$_3$): δ

1.28 (6H, s), 1.47 (3H, d, J~6.7 Hz), 1.65 (2H, m), 1.78 (2H, m), 2.74 (2H, t, J~6.3 Hz), 4.82(1H, q, J~6.7 Hz), 7.02 (1H,d,J~7.8 Hz), 7.08 (1H, dd, J~1.8 Hz, J~7.8 Hz), 7.32 (1H, d, J~1.8 Hz), and 1 [8,8-dimethyl (5,6,7,8-tetrahydronaphthalen)-3-yl] ethanol PMR (CDCl₃): δ 1.27(6H,s),147(3H,d,J~6.7 Hz), 1.65 (2H,m), 1.78(2H,m), 2.74(2H,t,J~6.3 Hz), 4.78(1H,q,J~6.7 Hz),7.02(1H,d,J~1.8 Hz), 7.11(1H,dd,J~8.1 Hz, J~1.8 Hz), 7.2(1H,d,J~8.1 Hz)

Methyl [8,8 dimethyl (5,6,7,8-tetrahydronaphthalen)-2-yl] ketone

To a stirred solution of 2.44 g (11.96 mmol) of 1-[8,8-dimethyl (5,6,7,8-tetrahydrodnapthalen)-2-yl] ethanol in 35 ml of methylene chloride was added 6.75 g (17.9 mmol) of pyridinium dichromate and 0.33 g (1.68 mmol) of pyridinium trifluroacetate at room temperature. The mixture was stirred for 16 hours and diluted with an equal volume of petroleum ether which caused a precipitate. The suspension was filtered through anhydrous MgSO₄ and silica gel (6 mm). Solvent was removed in-vacuo to give the title compound as a colorless liquid.

PMR(CDCl₃): δ 1.3 (6H,s), 1.67 (2H,m), 1.8 (2H,m), 2.55 (3H,s), 2.78 (2H,m), 7.08 (1H, d, J~8.0 Hz), 7.60 (1H, dd, J~8.0 Hz, J~1.8 Hz), 7.93 (1H, d, J~1.8 Hz).

Methyl [3,5,5,8,8-pentamethyl (5,6,7,8-tetrahydronaphthalen)-2-yl] ketone (Compound 30)

To a suspension of 6.71 g (50.3 mmol) of aluminum chloride in methylene chloride at 0° C. under argon was added a solution of 3.95 g (3.58 mL, 50.3 mmol) of acetyl chloride and 10.21 g (41.9 mmol) of 3,5,5,8,8-pentamethyl-5,6,7,8-tetrahydronaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, and dried (MgSO₄). Solvent was removed in-vacuo and the resulting residue purified using flash chromatography to give the title compound as an ivory solid.

PMR (CDCl₃): δ 1.28 (6H, s), 1.30 (6H, s), 1.69 (4H, s), 2.49 (3H, s), 2.57 (3H, s), 7.15 (1H, s), 7.67 (1H, s).

2-[3,5,5,8,8-pentamethyl-5,6,7,8-tetrahydronapthalen)-2-yl]-but-3-en-2-ol (Compound 31)

To a stirred solution of 5.36 g (21.9 mmol) of methyl [3,5,5,8,8-pentamethyl (5,6,7,8-tetrahydronapthalen)-2-yl] ketone (Compound 30) dissolved in 38 ml of freshly distilled tetrahydrofuran at 0° C. under argon was added 37.4 ml of 1.0M solution of vinyl magnesium bromide in tetrahydrofuran dropwise via syringe. The resulting mixture was allowed to warm to room temperature over a period of 2 hours with stirring. The mixture was recooled to 0° C. and saturated aqueous ammonium chloride solution was added dropwise. The mixture was then extracted with ether and the ether layers were washed with water, saturated sodium bicarbonate, brine, and dried (MgSO4). The solvent was removed in-vacuo and the residue purified using flash chromatography (SiO₂, 3% ethyl acetate in hexanes) to give the title compound as a white solid.

PMR (CDCl₃): δ 1.26(6H,s), 1.27 (6H,s), 1.66 (4H,s), 1.70(3H, s), 2.40 (3H,s), 5.14 (1H, dd, J~11 Hz, J~1.2 Hz), 5.23 (1H, dd, J~17 Hz, J~1.2 Hz), 6.16 (1H, dd, J~11 Hz, J~17 Hz), 7.04 (1H,s), 7.40 (1H,s).

Triphenyl [3-(5,6,7,8-tetrahydro-3,5,5,8,8-pentamethyl-2-naphthalenyl)-2-buten-yl] phosphonium bromide (E) (Compound 32)

To a solution of 6.30 g (18.4 mmol) of triphenylphosphonium hydrobromide in 50 ml of methanol was added 5.02 g (18.4 mmol) of 2-[3,5,5,8,8-pentamethyl-5,6,7,8-tetrahydronapthalen)-2-yl]-but-3-en-2-ol (Compound 31) in 50 ml of methanol via addition funnel dropwise at room temperature under argon. The solvent was removed in-vacuo after 16 hours of stirring and the residue was purified using flash chormatography (SiO₂, 5% methanol in methylene chloride) to give the title compound as a white foam.

PMR(CDCl₃): δ 1.21(6H,s),1.23(6H,s),1.63(4H,s), 1.80 (3H,d,J~6 Hz), 2.06(3H,m), 4.84(2H,m), 5.31(1H,s), 6.78 (1H,s), 7.0(1H,s), 7.65–7.97(15H,m).

2,5-Dichloro-2,5-dimethylhexane

Hydrogen chloride gas was bubbled through a suspension of 48 g (0.33 mol) of 2,5-dimethyl-2,5-hexanediol in 600 ml conc. hydrogen chloride until the solution was saturated. The resulting crystalline produce was collected by filtration, washed repeatedly with water and dried on a vacuum line to give the title compound as a crystalline white solid.

PMR (CDCl₃): δ 1.60 (12H, s), 1.94 (4H, s).

5,5,8,8-Tetramethyl-5,6,7,8-tetrahydronaphthalene

A vigorously stirred solution of 100 g (0.55 mol) of 2,5-dichloro-2,5-dimethylhexane in 300 ml benzene was cooled in an ice bath and treated with 45 g (0.34 mol) of anhydrous aluminum chloride in small portions. This mixture was stirred at room temperature for 3 hours, refluxed for 1 hour, cooled and poured into a mixture of ice and hydrogen chloride. The organic layer was recovered and the aqueous layer extracted with ether. Organic extracts were combined, washed with water, saturated Na₂CO₃ and saturated NaCl solutions and dried (MgSO₄).

After removing the solvent, the residue was fractionally distilled (78° C., 0.8 mm) to give the title compound as a colorless liquid.

PMR (CDCl₃): δ 1.3 (12H, s), 1.7 (4H, s), 7.1 (2H, m), 7.5 (2H, m).

Methyl [5,5,8,8-tetramethyl(5,6,7,8-tetrahydronaphthalen)-2-yl] ketone (Compound 33)

A suspension of 3.45 g (25.9 mmol) aluminum chloride in 15 ml methylene chloride was cooled under argon in an ice/salt bath and treated while stirring with a mixture of 4 g(21.2 mmol) 5,5,8,8-tetramethyl-5,6,7,8-tetrahydro naphthalene and 1.94 g (24.7 mmol) acetyl chloride via a dropping funnel over a period of 0.5 hours. Then the cooling bath was removed, the mixture stirred for 2 hours at room temperature and the reaction quenched with ice. The organic layer was recovered and the aqueous layer extracted with 2×50 ml methylene chloride.

The organic extracts were combined and washed with water, saturated NaHCO₃ solution and dried (MgSO₄). Solvent was removed in vacuo and the residue kugelrohr distilled (90° C.; 0.45 mm) to give the title compound as a colorless oil.

PMR (CDCl₃): δ 1.32 (6H, s), 1.33 (6H, s), 1.72 (4H, s), 2.60 (3H, s), 7.41 (1H, d, J~8.8 Hz), 7.71 (1H, dd, J~8.8, 2.6 Hz), 7.96 (1H, d, J~2.6 Hz).

2-[5,5,8,8-tetramethyl-(5,6,7,8-tetrahydronaphthalen)-2-yl]-2-but-3-enol (Compound 34)

To a stirred solution of 5.0 g (21.6 mmol) of freshly distilled (5,5,8,8-tetramethyl-(5,6,7,8-tetrahydronaphthalen)-2-yl] ketone (Compound 33) in 30 ml of tetrahydrofuran was added dropwise 43 ml (43.2 mmol) of vinyl magnesium bromide at 0° C. under argon. The solution was allowed to come to room temperature over a period of 72 hours with stirring. The mixture was quenched with saturated aqueous ammonium chloride and extracted with ether. The ether layers were washed with water, brine, and dried (MgSO$_4$). The solvent was removed in-vacuo and the residue purified using flash chromatography (Silica gel, 5% ethyl acetate in hexanes) to give the title compound as a yellow oil.

PMR (CDCl$_3$): δ 1.28 (6H,s), 1.30 (6H,s), 1.64 (3H,s), 1.68 (3H,s), 1.84 (1H,s), 5.32 (1H,d, J~17 Hz), 5.13 (1H,d, J~10 Hz), 6.18 (1H. dd, J~17 Hz, J~10 Hz), 7.2 (1H, dd J~2 Hz, J~8 Hz), 7.28 (1H,d,J~8 Hz), 7.4 (1H, d, J~2 Hz).

Triphenyl[3-(5,6,7,8-tetrahydro-5,5,8,8-tetramethyl-2-naphthalenyl)-2-butenyl-phosphonium bromide, (E) (Compound 35)

To a solution of 3.23 g (9.44 mmol) of triphenylphosphine hydrobromide in 30 ml of methanol was added 2.45 g (9.44 mmol) of 2-[5,5,8,8-tetramethyl-(5,6,7,8-tetrahydtronapthalen)-2-yl]-2-but-3-enol., (Compound 34) in 30 ml of methanol, dropwise at room temperature. The solvent was removed in-vacuo after 16 hours of stirring and the residue purified using flash chromatography (SiO$_2$, 5% methanol in methylene chloride) to give the title compound as an off-white solid.

PMR (CDCl$_3$): δ 1.23(6H,s), 1.25(6H,s), 1.64(3H,s), 1.65 (4H,s), 4.88(2H,dd,J~15 Hz, J~8.0 Hz), 5.54–5.62(1H,m), 6.93(1H,dd,J~8 Hz, J~2 Hz), 7.07(1H,d,J~2 Hz), 7.20(1H, d,J~8 Hz), 7.66–7.95(15H,m)

2-Carboethoxy-3-furaldehyde (Compound 40)

To a suspension of 7.02 g (68.7 mmol) of N,N'-trimethylethylene diamine in 100 ml of anhydrous tetrahydrofuran (chilled to –78° C.) was added 44.6 ml (71.4 mmol) of 1.6M n-BuLi in hexanes. A dark yellow solution was formed. The solution was stirred at –78° C. under a blanket of argon for 15 minutes. To the solution was added 6.24 g (64.9 mmol) of distilled 3-furaldehyde and the solution was stirred at –78° C. for 20 minutes. To this solution was added 55.0 ml (71.4 mmol) of 1.3M solution of BuLi in hexanes and the solution was stirred at –78° C. for 3 hours. The anion formed was transfered via cannula onto a solution of 7.75 g (6.8 ml, 71.4 mmol) of ethyl chloroformate in 20 ml of anhydrous tetrahydrofuran (chilled to –78° C.). The resulting solution was allowed to warm to room temperature and stirred overnight (16.33 h). The solution was poured onto 1:10 10% HCl: ice (v/v) and the layers were separated. The aqueous layer was extracted with ether and the organic phases combined, dried over MgSO$_4$, filtered and concentrated in vacuo to yield a brown oil. Purification by flash chromatography (silica gel, 5% ethyl acetate in hexane) yielded the title compound as a white solid.

PMR (CDCl$_3$): d 1.45 (3H, t, J=7.1 Hz), 4.47 (2H, q, J=7.1 Hz), 6.92 (1H, d, J=1.8 Hz), 7.56 (1H, d, 1.8 Hz), 10.55 (1H, s).

2-Methyl-3-thiophenecarboxylic acid

To a suspension of 5.32 g (41.5 mmol) of 3-thiophenecarboxylic acid in 100 ml of anhydrous tetrahydrofuran (chilled to –78° C.) was added 57.1 ml (91.4 mmol) of 1.6M n-BuLi in hexanes. The cloudy suspension was stirred at –78° C. under a blanket of argon for 40 minutes, and was then transfered via canulla onto a solution of 59.05 g (25.9 ml, 416 mmol) of methyl iodide dissolved in 20 ml of anhydrous tetrahydrofuran (chilled to –78° C.). The resulting clear, colorless solution was allowed to warm to room temperature and stirred for 20 hours. A white solid was formed. The reaction mixture was concentrated in vacuo, partitioned between 75 ml of sat. NH$_4$Cl solution and 150 ml of ethyl ether, and the layers separated. The aqueous phase was washed with 100 ml of ethyl ether and layered with 100 ml of ethyl ether and acidified with 1N sulfuric acid solution until all of the yellow emulsion dissapated. All organic phases were combined, washed with brine solution, dried over MgSO$_4$, filtered and concentrated in vacuo to yield an off-white solid. Purification by flash chromatography (silica gel, 75% ethyl acetate in hexane) yielded the title compound as an off white solid.

PMR (CDCl$_3$): d 2.78 (3H, s), 7.01 (1H, d, J=5.4 Hz), 7.45 (1H, d, 5.4 Hz).

Methyl (2-methyl)3-thiophenecarboxylate

To a solution of 3.30 g (23.2 mmol) of 2-methyl-3-thiophenecarboxylic acid in 100 ml of acetone was added 16.04 g (116.1 mmol) of anhydrous potassium carbonate and 16.47 g (7.2 ml, 116.1 mmol) of methyl iodide. The reaction mixture was allowed to stir at room temperature for 20.25 hours. A white precipitate formed. The white precipitate was filtered, washed with ethyl ether and discarded. The filtrate was concentrated in vacuo, partitioned between 250 ml of water and 250 ml of pentane and the layers separated. The organic phase was washed with a saturated solution of Na$_2$SO$_3$, dried over Na$_2$SO$_4$, filtered and concentrated by rotary evaporation to give the title compound as a yellow oil which was used without further purification.

PMR (CDCl$_3$): d 2.74 (3H, s), 3.85 (3H, s), 6.98 (1H, d, J=5.4 Hz), 7.38 (1H, d, 5.4 Hz).

Methyl 3-[2-(imino-(N-oxide)-4-N,N-dimethylaniline)]thiophenecarboxylate

To a suspension of 3.79 g (24.3 mmol) of methyl (2-methyl)3-thiophenecarboxylate in 55 ml of CCl$_4$ was added 5.18 g (29.1 mmol) of N-bromosuccinimide and 0.06 g (0.24 mmol) of benzoyl peroxide. A heterogeneous yellow mixture was formed. The mixture was refluxed for 3 hours and turned dark orange in color. The mixture was allowed to stir at room temperature overnight. To the mixture was added 1.28 g (7.2 mmol) of N-bromosuccinimide and then the mixture was warmed to reflux for 3 hours. A white solid precipitate was removed by filtration, and the resulting solution was washed with cold 15% NaOH solution (w/v) and cold water. The organic fraction was diluted with 100 ml of CCl$_4$ and was dried over NaSO$_4$, filtered and concentrated in vacuo to yield a yellow oil. Purification by flash chromatography (silica gel, 2% ethyl acetate in hexane) yielded methyl 3-(2-methylbromo)thiophenecarboxylate as a yellow oil. 1.76 g (7.5 mmol) of this crude thiophenecarboxylate was dissolved in 20 ml of CCl$_4$ and 2.0 ml (24.7 mmol) of pyridine was added. The solution was heated to 85° C. for 1 hour and then concentrated in vacuo to yield a solid residue. The residue was dissolved in 20 ml of methanol and added to a solution of 4-nitrosodimethylaniline in 30 ml of methanol chilled to 0° C. The solution was allowed to stir a few minutes. 11.3 ml (11.3 mmol) of 1N NaOH solution was added to the dark green solution, and the solution was stirred at 0° C. for 1 hour. An orange precipitate formed. The suspension was stored at −10° C. overnight to induce further precipitation. The orange solid was collected by filtration, washed with 200 ml of water and dried in vacuo to yield the title compound as an orange solid.

PMR (CDCl$_3$): d 3.05 (6H, s), 3.93 (3H, s), 6.71 (2H, d, J=9.2 Hz), 7.37 (1H, d, 5.4 Hz), 7.64 (1H, d, 5.4 Hz), 7.80 (2H, d, J=9.2 Hz), 9.70 (1H, s).

3-Carbomethoxy-2-thiophenecarboxaldehyde (Compound 41)

To a 1:1 mixture of 1N H$_2$SO$_4$ and ethyl ether cooled to 0° C. was added 0.94 g (3.09 mmol) of methyl 3-[2-(imino-(N-oxide)-4-N,N-dimethylaniline)]thiophenecarboxylate in several portions over a 15 minute period. The suspension was allowed to stir at 0° C. for 1 hour. A clear, biphasic mixture formed. The layers were separated and the aqueous phase was washed once with 100 ml of ethyl ether. The organic fractions were combined, washed once with 75 ml of brine, dried over Na$_2$SO$_4$, filtered and concentrated in vacuo to yield the title compound as an orange solid which was used without further purification.

PMR (CDCl$_3$): d 3.96 (3H, s), 7.59 (1H, d, 4.9 Hz), 7.64 (1H, dd, J=4.9 , 1.1 Hz), 10.63 (1H, d, J=1.1 Hz).

3-Carbomethoxy-2-furaldehyde (Compound 42)

This compound was prepared substantially in accordance with the literature procedure of M. Valenta, Collect. Czech. Chem. Commun. 1969, (6)1814–18.

2-Carbomethoxybenzaldehyde (Compound 43)

4.5 g (30 mmol) of 2-carboxybenzaldehyde, 17.1 g (120 mmol) of iodomethane and 12.4 g (90 mmol) of potassium carbonate were stirred in 85 ml of acetone for 24 hours. The solvent was removed by evaporation and the residue was partioned between 50 ml of water and 50 ml of ether. The aqueous layer was washed with 3×50 ml portions of ether. The combined organic extracts were washed with 30 ml each of 1M sodium thiosufate and saturated sodium cloride solutions and dried over MgSO$_4$. The solvent was removed by evaporation. The residue was subjected to flash chromatography (silica gel, 10% ethyl acetate/hexanes) to give the title compound as a clear colorles oil.

PMR (CDCl$_3$): d 3.98 (3H, s), 7.65–7.68 (2H, m), 7.94–8.00 (2H, m), 10.63 (1H, s).

2-Carboethoxybenzaldehyde. (Compound 44)

Using the same procedure as for the preparation of 2-carbomethoxybenzaldehyde (Compound 43), but instead using 5.0 g (33 mmol) of 2-carboxybenzaldehyde, 23.4 g (150 mmol) of iodoethane and 13.8 g (100 mmol) of K$_2$CO$_3$ gave the title compound as a clear colorless oil.

PMR (CDCl$_3$): d 1.42 (3H, t, J=7.1 Hz), 4.45 (2H, q, J=7.1 Hz), 7.64–7.67 (2H, m), 7.92–8.00 (2H, m).

3-(1,3-dioxolane-2-yl)-thiophene

A solution of 28.04 g (250 mmol) of 3-thiophenecarboxaldehyde, 20.2 g (330 mmole) of ethyleneglycol, 10 mg (0.05 mmole) of p-toluenesulfonic acid monohydrate and 25 ml of benzene was heated to reflux untill the calculated amount of water was removed via a Dean-Stark trap (5 hours). The reaction mixture was allowed to cool to room temperature and was washed with 30 ml of saturated NaHCO$_3$ solution. The organic layer was dried over MgSO$_4$ and the solvent was removed by evaporation to give the title compound as a clear colorles oil.

PMR (CDCl$_3$): d 3.98–4.15 (4H, m), 5.98 (1H, s), 7.16 (1H, dd, J=5.0, 1.2 Hz), 7.32 (1H, dd, J=5.0, 3.0 Hz), 7.42 (1H, dd, J=3.0, 1.2).

2-Carboethoxy-3-thiophenecarboxaldehyde (45)

To a solution of 5.0 g (32 mmole) of 3-(1,3-dioxolane-2)-thiophene in 20 ml of ethyl ether was added 22 ml (35 mmole) of n-butyl lithium (1.6M in hexanes). The reaction was warmed to reflux for 15 minutes. The solution was then cooled to 0° C. and transfered via canulla into a chilled (0° C.) solution of 3.9 g (35 mmole) of ethyl chloroformate in 20 ml of ethyl ether. This solution was allowed to warm to room temperature and was added to 20 ml of saturated sodium chloride solution. The organic layer was separated, the solvent was removed by evaporation and the residue was dissolved in 20 ml of tetrahydrofuran. 10 ml of 10% HCl solution was added and the solution and was stirred at reflux for 24 hours. The majority of the solvent was removed by evaporation and the residue was partitoned between 30 ml of ethyl ether and 30 ml of saturated NaHCO$_3$ solution. The ether layer was washed with saturated NaCl solution, dried over MgSO$_4$ and the solvent was removed by evaporation to yield the title compound as a clear yellow oil.

PMR (CDCl$_3$); d 1.43 (3H, t, J=6.1 Hz), 4.43 (2H, q, J=6.1 Hz), 7.46 (1H, d, J=5.0 Hz), 7.59 (1H, d, J=5.0 Hz), 10.66 (1H, s).

Methyl 2-[4-methyl-4-(3,5,5,8,8-pentamethyl-5,6,7, 8-tetrahydronaphthalene)-2-yl-1E,3E-butadien-1-yl]-furan-3-carboxylate (Compound 1)

A suspension of 1.5 g (2.51 mmol) of [(5,6,7,8-tetrahydro-3,5,5,8,8-pentamethylnaphthalene-2-yl)but-3-ene-1-yl] triphenylphosphonium bromide (Compound 32), 387 mg (2.51 mmol) of 3-carbomethoxy-2-furaldehyde (Compound 42) and 7 ml of 1,2-epoxybutane were combined under argon and warmed to reflux for 24 hours. The resulting solution was concentrated in vacuo and the residue purified using flash chromatography (silica gel, 10% ethtyl acetate in hexanes) to give a mixture of geometric isomers. To increase the yield of trans isomer about the disubstituted double bond, a solution of the isomeric mixture in 30 ml toluene and 40 ml ether was treated with 30 mg (0.01 mmol) of iodine and stirred under argon for 24 hours. The solvent was removed by evaporation and the residue was purified by flash chromatography (silica gel, 10% ethyl acetate in hexanes). Isomers were separated by reverse phase HPLC (Partisil ODS-2; 11% H$_2$O in acetonitrile) to give the title compound as a clear pale yellow oil.

PMR (CDCl$_3$); d 1.26 (12H, S), 1.67 (4H, s), 2.20 (3H, d, J=1.0 Hz), 2.26 (3H, s), 3.84 (3H, s), 6.20 (1H, dd, J=11.5, 1.0 Hz), 6.72, 1H, d, J=1.9 Hz), 7.06 (1H, s), 7.07 (1H, d, J=15.6 Hz), 7.10 (1H, s), 7.30 (1H, d, J=1.9 Hz), 7.35 (1H, dd, J=11.5, 15.6 Hz).

Methyl 2-[4-methyl-4-(3,5,5,8,8-pentamethyl-5,6,7, 8-tetrahydronaphthalene)-2-yl-1E,3Z-butadien-1-yl]-furan-3-carboxylate (Compound 2)

Using the same procedures as for the preparation of methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1), the title compound was obtained as a clear pale yellow oil.

PMR (CDCl$_3$); d 1.25 (6H, s), 1.30 (6H, s), 1.69 (4H, s), 2.12 (3H, s), 2.16 (3H, s), 3.83 (3H, s), 6.34 (1H, d, J=11

Hz), 6.64 (1H, d, J=2 Hz), 6.65 (1H, dd, J=11, 16 Hz), 6.97 (1H, s), 7.00 (1H, d, J=16 Hz), 7.11 (1H, s), 7.16 (1H, d, 2 Hz).

Ethyl 2-[4-methyl-4-(3,5,5,8,8-pentamethyl-5,6,7,8-tetrahydronaphthalene)-2-yl-1E,3E-butadien-1-yl] benzoate (Compound 3)

Using the same procedures as for the preparation of methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1) but instead using 7.50 g (12.5 mmol) of [(5,6,7,8-tetrahydro-3,5,5,8,8-pentamethylnaphthalene-2-yl)but-3-ene-1-yl] triphenylphosphonium bromide (Compound 32) and 2.47 g of 2-carboethoxy benzaldehyde (Compound 44) suspended in 30 ml of 1,2-epoxybutane, gave the title compound as a clear pale yellow oil.

PMR (CDCl$_3$); d 1.28 (6H,s), 1.29 (6H, s), 1.39(3H, t, J=7.1 Hz), 1.68 (4H, s), 2.17 (3H, s), 2.27 (3H, s), 4.35 (2H, q, J=7.1 Hz), 6.21 (1H, d, J=11.1 Hz), 7.05 (1H, s), 7.07 (1H, dd, J=11.1, 15.4 Hz), 7.09 (1H,s), 7.29 (1H,dd, J=1.6, 7.8 Hz), 7.34 (1H, d, J=15.4 Hz), 7.45–7.50 (1H, m), 7.70 (1H, d, J=7.3 Hz), 7.86 (1H, dd, J=1.6, 7.8 Hz).

Ethyl 2-[4-methyl-4-(3,5,5,8,8-pentamethyl-5,6,7,8-tetrahydronaphthalene)-2-yl-1E,3Z-butadien-1-yl] benzoate (Compound 4).

Using the procedure as for the preparation of ethyl 2-[4-methyl-4-(3,5,5,8,8-pentamethyl-5,6,7,8-tetrahydronaphthalene)-2-yl-1E,3E-butadien-1-yl]benzoate (Compound 3), the title compound was isolated as a colorless oil.

PMR (CDCl$_3$): d 1.26 (6H, s), 1.29 (6H,s), 1.37 (3H, t, J=7.1 Hz), 1.69 (4H, s), 2.08 (3H, s), 2.16 (3H,s), 4.33 (2H, q, J=7.1 Hz), 6.32–6.45 (2H,m), 6.99 (1H, s), 7.10 (1H, s), 7.15–7.22 (1H, m), 7.31–7.35 (3H, m), 7.80 (1H, d, J=7.2 Hz).

Methyl 2-[4-methyl-4-(5,5,8,8-tetramethyl-5,6,7,8-tetrahydronaphthalene)-2-yl-1E,3Z-butadien-1-yl] benzoate (Compound 5)

Using the same procedures as for the preparation of methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1), but instead using 1.5 g (2.57 mmol) of [(5,6,7,8-tetrahydro-5,5,8,8-tetramethylnaphthalene-2-yl)but-3-ene-1-yl] triphenylphosphonium bromide (Compound 35) and 422 mg (2.57 mmole) of 2-carbomethoxy benzaldehyde (Compound 43) gave the title compound as a clear pale yellow oil.

PMR (CDCl$_3$); d 1.31 (12H, s), 1.69 (4H, s), 2.18 (3H, s), 3.89 (3H, s), 6.36 (1H, d, J=11.1 Hz), 6.96 (1H, dd, 15.6, 11.1 Hz), 7.07 (1H, dd, J=8.1 , 1.9 Hz), 7.15–7.21 (1H, m), 7.26 (1H, d, J=1.7 Hz), 7.29 (1H, d, J=8.1 Hz), 7.28–7.33 (1H, m), 7.38 (1H, d, J=15.6 Hz), 7.49 (1H, d, J=8.1 Hz), 7.81 (1H, dd, J=7.8, 1.4 Hz).

Methyl 2-[4-methyl-4-(5,5,8,8-tetramethyl-5,6,7,8-tetrahydronaphthalene)-2-yl-1E,3E-butadien-1-yl] benzoate (Compound 6)

Using the same procedures as for the preparation of methyl 2-[4-methyl-4-(5,5,8,8-tetramethyl-5,6,7,8-tetrahydronaphthalene)-2-yl-1E,3Z-butadien-1-yl]benzoate (Compound 5) gave the title compound as a clear pale yellow oil.

PMR (CDCl$_3$); d 1.28 (6H, s), 1.32 (6H, s), 1.68 (4H, s), 2.25 (3H, s), 3.87 (3H, s), 6.71 (1H, d, J=10.2), 7.24 (1H, dd, J=15.2, 10.2 Hz), 7.22–7.28 (3H, m), 7.41–7.45 (2H, m), 7.52 (1H, d, J=15.2 Hz), 7.69 (1H, d, J=7.5 Hz), 7.86 (1H, dd, J=7.5, 1.4 Hz).

2-[4-Methyl-4-(3,5,5,8,8-pentamethyl-5,6,7,8-tetrahydronaphthalene)-2-yl-1E,3E-butadien-1-yl] benzoic acid (Compound 7)

610 mg (1.52 mmol) of ethyl 2-[4-methyl-4-(3,5,5,8,8-pentamethyl-5,6,7,8-tetrahydronaphthalene)-2-yl-1E,3E-butadien-1-yl]benzoate (Compound 3) was suspended in 5ml of tetrahydrofuran and 6.1 ml of 0.5M LiOH solution (3.0 mmol). The suspension was warmed to reflux for 18 hours. The solution was evaporated to dryness. The residue was dissolved in 250 ml H$_2$O and washed with 100 ml of ethyl ether. To the aqueous layer was added 100 ml of ethyl ether and brought to pH=1 with 12M HCl. The aqueous layer was washed with more ethyl ether (3×100 ml). The organic fractions were combined, washed with brine, dried over MgSO$_4$, and evaporated to give the title compound as a white solid.

PMR (d$_6$-DMSO); d 1.23 (12H, s), 1.62 (4H, s), 2.15 (3H, s), 2.20 (3H, s), 6.08 (1H, d, J=10.4 Hz), 7.03 (1H, s), 7.11 (1H, s), 7.18 (1H, dd, J=16.6, 10.4 Hz), 7.31 (1H, d, J=16.6 Hz), 7.32–7.36 (1H, m), 7.51–7.57 (1H, m), 7.77 (1H, dd, J=7.8, 1.2 Hz), 7.88 (1H, d, J=7.8 Hz).

2-[4-Methyl-4-(3,5,5,8,8-pentamethyl-5,6,7,8-tetrahydronaphthalene)-2-yl-1E,3Z-butadien-1-yl] benzoic acid (Compound 8)

Using the same procedure as for the preparation of 2-[4-methyl-4-(3,5,5,8,8-pentamethyl-5,6,7,8-tetrahydronaphthalene)-2-yl-1E,3E-butadien-1-yl]benzoic acid (Compound 7) but instead using 0.5 g (1.2 mmol) of ethyl 2-[4-methyl-4-(3,5,5,8,8-pentamethyl-5,6,7,8-tetrahydronaphthalene)-2-yl-1E,3Z-butadien-1-yl]benzoate (Compound 5), 5 ml of tetrahydrofuran, and 5 ml 0.5M LiOH (2.5 mmol), gave the title compound as a white solid.

PMR (CDCl$_3$); d 1.27 (6H, s), 1.30 (6H, s), 1.69 (4H, s), 2.12 (3H, s), 2.19 (3H, s), 6.38–6.49 (2H, m), 7.00 (1H, s), 7.11 (1H, s), 7.20–7.25 (1H, m), 7.38–7.43 (3H, m), 7.97 (1H, d, J=1.2 Hz).

2-[4-Methyl-4-(3,5,5,8,8-pentamethyl-5,6,7,8-tetrahydronaphthalene)-2-yl-1E,3Z-butadien-1-yl]-furan-3-carboxylic acid (Compound 9)

Using the same procedures as for the preparation of 2-[4-methyl-4-(3,5,5,8,8-pentamethyl-5,6,7,8-tetrahydronaphthalene)-2-yl-1E,3E-butadien-1-yl]benzoic acid (Compound 7), but instead using 266 mg (0.69 mmol) of methyl 2-[4-methyl-4-(3,5,5,8,8-pentamethyl-5,6,7,8-tetrahydronaphthalene)-2-yl-1E,3Z-butadien-1-yl]-furan-3-carboxylate (Compound 2), 5.5 ml of tetrahydrofuran and 2.75 ml of 0.5M LiOH (1.37 mmol), gave the title compound as a white solid.

PMR (CDCl$_3$); d 1.26 (6H, s), 1.31 (6H, s), 1.70 (4H, s), 2.14 (3H, s), 2.17 (3H, s), 6.36 (1H, d, J=11.3 Hz), 6.70 (1H, dd, J=15.6, 11.3 Hz), 6.72 (1H, d, J=2.0 Hz), 6.98 (1H, s), 7.04 (1H, d, J=15.6 Hz), 7.13 (1H, s), 7.19 (1H, d, J=2.0 Hz).

2-[4-Methyl-4-(3,5,5,8,8-pentamethyl-5,6,7,8-tetrahydronaphthalen)-2-yl-1E,3E-butadien-1-yl] furan 3-carboxylic acid (Compound 10

Using the same procedures as for the preparation of 2-[4-methyl-4-(3,5,5,8,8-pentamethyl-5,6,7,8- tetrahydronaphthalene)-2-yl-1E,3E-butadien-1-yl]benzoic acid (Compound 7), but instead using 480 mg (1.27 mmol) of compound methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1), 10 ml of tetrahydrofuran and 5.0 ml of 0.5M LiOH (2.50 mmol), gave the title compound as a white solid.

PMR (CDCl$_3$); d 1.28 (6H, s),1.29 (6H, s), 1.68 (4H, s), 2.21 (3H, s), 2.25 (3H, s), 6.20(1H, d, J=12.0 Hz), 6.77 (1H, d, J=1.9 Hz), 7.05 (1H, s), 7.08 (1H, d, J=15.0 Hz), 7.09 (1H, s), 7.33 (1H, d, J=1.9 Hz), 7.38 (1H, dd, J=15.0, 12.0 Hz).

Methyl 2-[4-methyl-4-(5,5,8,8-tetramethyl-5,6,7,8-tetrahydronaphthalen)-2-yl-1E,3E-butadien-1-yl] furan 3-carboxylate (Compound 11)

Using the same procedure as for the preparation of methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1), but instead using 2.53 g (4.34 mmol) of [(5,6,7,8-tetrahydro- 5,5,8,8-tetramethylnaphthalene-2-yl ) but-3-ene-1-yl] triphenylphosphonium bromide (Compound 35) and 0.67 g (4.34 mmol) of 3-carbomethoxy-2-furaldehyde (Compound 42) suspended in 30 ml of 1,2-epoxybutane, gave the title compound as a clear colorless oil.

PMR (CDCl$_3$); d 1.29 (6H, s), 1.33 (6H, s), 1.70 (4H, s), 2.28 (3H, s), 3.86 (3H, s), 6.68 (1H, d, J=11.5 Hz), 6.72 (1H, d, J=2.0 Hz), 7.15 (1H, d, J=15.5 Hz), 7.25–7.31 (3H, m), 7.40 (1H, dd, J=11.5, 15.5 Hz), 7.45 (1H, s).

Methyl 2-[4-methyl-4-(5,5,8,8-tetramethyl-5,6,7,8-tetrahydronaphthalen)-2-yl-1E, 3Z-butadien-1-yl] furan 3-carboxylate (Compound 12)

Using the same procedure as for the preparation of methyl 2-[4-methyl-4-(5,5,8,8-tetramethyl-5,6,7,8-tetrahydronaphthalen)-2-yl-1E, 3E-butadien-1-yl] furan 3-carboxylate (Compound 11) gave the title compound as a clear colorless oil.

PMR (CDCl$_3$); d 1.30 (6H, s), 1.31 (6H, s), 1.71 (4H, s), 2.21 (3H, s), 3.84 (3H, s), 6.33 (1H, d, J=11.5 Hz), 6.66 (1H, d, J=2.0 Hz), 7.03 (1H, d, J=15.8 Hz), 7.07 (1H, dd, J=2.0, 8.6 Hz), 7.15 (1H, dd, J=11.5, 15.8 Hz), 7.16 (1H, d, J=2.0 Hz), 7.23 (1H, d, J=2.0 Hz), 7.30 (1H, d, J=8.6 Hz).

2-[4-Methyl-4-(5,5,8,8-tetramethyl-5,6,7,8-tetrahydronaphthalen)-2-yl-1E, 3E-butadien-1-yl] furan 3-carboxylic acid (Compound 13)

710 mg (1.9 mmol) of methyl 2-[4-methyl-4-(5,5,8,8-tetramethyl-5,6,7,8-tetrahydronaphthalen)-2-yl-1E, 3E-butadien-1-yl] furan 3-carboxylate (Compound 11) was suspended in 20 ml of tetrahydrofuran and 2.0 ml of 2N KOH solution (3.0 mmol). The suspension was stirred at room temperature for 24 hours. The solution was evaporated to dryness. The residue was dissolved in 250 ml H$_2$O and washed with 100 ml of ethyl ether. To the aqueous fraction was added 100 ml of ethyl ether and brought to pH=1 with 12M HCl. The aqueous layer was washed with ethyl ether (3×100 ml). The organic fractions were combined, washed with brine, dried over MgSO$_4$, and evaporated to give the title compound as a white solid.

PMR (CDCl$_3$); d 1.30 (6H, s), 1.34 (6H, s), 1.71 (4H, s), 2.26 (3H, s), 6.71 (1H, d, J=11 Hz), 6.78 (1H, d, J=2 Hz), 7.16 (1H, d, J=15.5 Hz), 7.25–7.31 (3H, m), 7.45 (1H, dd, J=11, 15.5 Hz), 7.46(1H, s).

2-[4-Methyl-4-(5,5,8,8-tetramethyl-5,6,7,8-tetrahydronaphthalen)-2-yl-1E,3Z-butadien-1-yl] furan 3-carboxylic acid (Compound 14)

Using the same procedure as for the preparation of 2-[4-methyl-4-(5,5,8,8-tetramethyl-5,6,7,8-tetrahydronaphthalen)-2-yl-1E,3E-butadien-1-yl] furan 3-carboxylic acid (Compound 13), but instead using 120 mg (0.32 mmol) of methyl 2-[4-methyl-4-(5,5,8,8-tetramethyl-5,6,7,8-tetrahydronaphthalen)-2-yl-1E,3Z-butadien-1-yl] furan 3-carboxylate (Compound 12) gave the title compound as a white solid.

PMR (CDCl$_3$); d 1.31 (6H, s) , 1.32 (6H, s), 1.72 (4H, s), 2.23 (3H, s), 6.36 (1H, d, J=11.5 Hz), 6.71 (1H, d, J=2.0 Hz), 7.07 (1H, d, J=15.8 Hz), 7.08 (1H, dd, J=2.0, 8.6 Hz), 7.18–7.24 (3H, m), 7.30 (1H, d, J=8.5 Hz).

Ethyl 3-[4-methyl-4-(3,5,5,8,8-pentamethyl-5,6,7,8-tetrahydronaphthalen)-2-yl-1E,3E-butadien-1-yl] thiophene 2-carboxylate (Compound 15)

Using the same procedures as for the preparation of methyl 2-[4-methyl-4-(3,5,5,8,8-pentamethyl-5,6,7,8-tetrahydronaphthalene)-2-yl-1E,3E-butadien-1-yl]-furan-3-carboxylate (Compound 1), but instead using 3.56 g (5.98 mmol) of [(5,6,7,8-tetrahydro-3,5,5,8,8-pentamethylnaphthalene-2-yl)but-3-ene-1-yl] triphenylphosphonium bromide (Compound 32) and 1.1 g (5.98 mmol) of 2-carboethoxy-3-thiophenecarboxaldehyde (Compound 45) suspended in 20 ml of 1,2-epoxybutane, gave the title compound as a clear pale yellow oil.

PMR (CDCl$_3$); d 1.28 (6H, s), 1.29 (6H, s), 1.37 (3H, t, J=7.1 Hz), 1.68 (4H, s), 2.17 (3H, s), 2.26 (3H, s),4.33 (2H, q, J=7.1 Hz), 6.21 (1H, d, J=11.5 Hz), 7.06 (1H, s), 7.09 (1H, s), 7.14 (1H, dd, J=11.5, 15.5 Hz), 7.40 (1H, d, J=5.3 Hz), 7.42 (1H, d, J=5.3 Hz), 7.52 (1H, d, J=15.5 Hz).

Ethyl 3-[4-methyl-4-(3,5,5,8,8-pentamethyl-5,6,7,8-tetrahydronaphthalen)-2-yl-1E,3Z-butadien-1-yl] thiophene 2-carboxylate (Compound 16)

Using the same procedures as for the preparation of ethyl 3-[4-methyl-4-(3,5,5,8,8-pentamethyl-5,6,7,8-tetrahydronaphthalen)-2-yl-1E,3E-butadien-1-yl] thiophene 2-carboxylate (Compound 15), gave the title compound as a clear yellow oil.

PMR (CDCl$_3$); d 1.25 (6H, s), 1.31 (6H, s), 1.38 (3H, t, J=7.1 Hz), 1.69 (4H, s), 2.11 (3H, s), 2.16 (3H, s),4.34 (2H, q, J=7.1 Hz), 6.35 (1H, d, J=10.9 Hz), 6.45 (1H, dd, J=10.9, 15.3 Hz), 6.97 (1H, s), 7.01 (1H, d, J=5.3 Hz), 7.11 (1H, s), 7.26 (1H, d, J=5.3 Hz), 7.52 (1H, d, J=15.3 Hz).

3-[4-Methyl-4-(3,5,5,8,8-pentamethyl-5,6,7,8-tetrahydronaphthalen)-2-yl-1E,3E-butadien-1-yl] thiophene 2-carboxylic acid (Compound 17)

Using the same procedure as for the preparation of 2-[4-methyl-4-(3,5,5,8,8-pentamethyl-5,6,7,8-tetrahydronaphthalene)-2-yl-1E,3E-butadien-1-yl]benzoic acid (Compound 7), but instead using 525 mg (1.2 mmol) of ethyl 3-[4-methyl-4-(3,5,5,8,8-pentamethyl-5,6,7,8-tetrahydronaphthalen)-2-yl-1E,3E-butadien-1-yl] thiophene 2-carboxylate (Compound 15), 5 ml of tetrahydrofuran, and 5 ml 0.5M LiOH (2.5 mmol), gave the title compound as a white solid.

PMR (CDCl$_3$); d 1.23 (6H, s), 1.24 (6H, s), 1.62 (4H, s), 2.16 (3H, s), 2.20 (3H, s), 6.07 (1H, d, J=9.5 Hz), 7.03 (1H, s), 7.12 (1H, s), 7.33 (1H, dd, J=9.5, 15.5 Hz), 7.43 (1H, d, J=15.5 Hz), 7.74 (1H, d, J=5.4 Hz), 7.77 (1H, d, J=5.4 Hz).

3-[4-Methyl-4-(3,5,5,8,8-pentamethyl-5,6,7,8-tetrahydronaphthalen)-2-yl-1E,3Z-butadien-1-yl] thiophene 2-carboxylic acid (Compound 18)

Using the same procedure as for the preparation of 2-[4-methyl-4-(3,5,5,8,8-pentamethyl-5,6,7,8- tetrahydronaphthalene)-2-yl-1E,3E-butadien-1-yl]benzoic acid (Compound 7) but instead using 113 mg (0.27 mmol) of ethyl 3-[4-methyl-4-(3,5,5,8,8-pentamethyl-5,6,7,8-tetrahydronaphthalen)-2-yl-1E,3Z-butadien-1-yl] thiophene 2-carboxylate (Compound 16), 5 ml of tetrahydrofuran, and 5 ml 0.5M LiOH (2.5 mmol), gave the title compound as a white solid.

PMR (CDCl₃); d 1.26 (6H, s), 1.32 (6H, s),1.70 (4H, s), 2.13 (3H, s), 2.17 (3H, s), 6.38 (1H, d, J=11 Hz), 6.50 (1H, dd, J=11, 15.3 Hz), 7.00 (1H, s), 7.05 (1H, d, J=5.3 Hz), 7.12 (1H, s), 7.37 (1H, d, J=5.3 Hz), 7.45 (1H, d, J=15.3 Hz).

Ethyl 3-[4-methyl-4-(3,5,5,8,8-pentamethyl-5,6,7,8-tetrahydronaphthalene)-2-yl-1Z,3E-butadiene-1yl]-2-furanoate (Compound 19)

A suspension of 3.68 g (6.2 mmol) of [(5,6,7,8-tetrahydro-3,5,5,8,8-pentamethylnaphthalene-2-yl)but-3-ene-1-yl] triphenylphosphonium bromide (Compound 32), 0.69 g (4.1 mmol) of 2-carboethoxy-3-furaldehyde (Compound 40) and 35 ml of 1,2-epoxybutane were combined under argon and warmed to reflux for 14.5 hours. The resulting solution was concentrated in vacuo and the residue purified by flash chromatography (silica gel, 3% ethyl acetate in hexane) to give the title compound as an off-white solid. Further amounts of the compound were isolated from impure chromatography fractions by normal phase HPLC (Parisil 10, 1% ethyl acetate in hexane).

PMR (CDCl₃): d 1.26 (6H, s), 1.29 (6H, s), 1.41 (3H, t, J=7.1 Hz), 1.67 (4H, s), 2.15 (3H, s), 2.25 (3H, s), 4.39 (2H, q, J=7.1 Hz), 6.46 (1H, d, J=11.7 Hz), 6.69 (1H, dd, J=11.7, 11.3 Hz), 6.72 (1H, d, J=1.8 Hz), 6.88 (1H, d, J=11.3 Hz), 7.03 (1H, s), 7.09 (1H, s), 7.44 (1H, d, J=1.8 Hz).

Methyl 2-[4-methyl-4-(3,5,5,8,8-pentamethyl-5,6,7,8-tetrahydronaphthalene)-2-yl-1Z,3E-butadiene-1-yl]-3-thiophenecarboxylate (Compound 20)

Using the same procedure as for the preparation of ethyl 3-[4-methyl-4-(3,5,5,8,8-pentamethyl-5,6,7,8-tetrahydronaphthalene)-2-yl-1Z,3E-butadiene-1-yl]-2-furanoate (Compound 19), but instead using 2.42 g (4.05 mmol) of [(5,6,7,8-tetrahydro-3,5,5,8,8-pentamethylnaphthalene-2-yl)but-3-ene-1-yl] triphenylphosphonium bromide (Compound 32) and 0.46 g (2.7 mmol) of 3-carbomethoxy-2-thiophenecarboxaldehyde (Compound 41) suspended in 30 ml of 1,2-epoxybutane refluxed for 19 hours yielded a mixture of isomers. Purification by flash chromatography (silica, 2% ethyl acetate in hexane) yielded a mixture of geometric isomers. Isomers were purified by normal phase HPLC (Partisil 10 PAC, 1% ethyl acetate in hexane) to give the title compound as a yellow foamy solid.

PMR (CDCl₃): d 1.27 (6H, s), 1.29 (6H, s), 1.67 (4H, s), 2.18 (3H, s), 2.28 (3H, s), 3.86 (3H, s), 6.76 (1H, d, J=12.0 Hz), 6.69 (1H, dd, J=12.0, 10.3 Hz), 7.09 (2H, s), 7.14 (1H, d, J=5.4 Hz), 7.39 (1H, d, J=10.3 Hz), 7.43 (1H, d, J=5.4 Hz).

Methyl 2-[4-methyl-4-(3,5,5,8,8-pentamethyl-5,6,7, 8-tetrahydronaphthalene)-2-yl-1E,3E-butadiene-1-yl]-3-thiophenecarboxylate (Compound 21)

Using the same procedure as for the preparation of methyl 2-[4-methyl-4-(3,5,5,8,8-pentamethyl-5,6,7,8-tetrahydronaphthalene)-2-yl-1Z,3E-butadiene-1-yl]-3-thiophenecarboxylate (Compound 20) the title compound was obtained as a yellow foamy solid.

PMR (CDCl₃): d 1.28 (6H, s), 1.29 (6H, s), 1.68 (4H, s), 2.18 (3H, s), 2.26 (3H, s), 3.85 (3H, s), 6.20 (1H, d, J=11.6 Hz), 7.04 (1H, d, J=4.8 Hz), 7.05 (1H, s), 7.09 (1H, s), 7.12 (1H, dd, J=11.6, 15.5 Hz), 7.39 (1H, d, J=5.4 Hz), 7.60 (1H, d, J=15.5 Hz).

2-[4-methyl-4-(3,5,5,8,8-pentamethyl-5,6,7,8-tetrahydronaphthalene)-2-yl-1E,3E-butadiene-1-yl]-3-thiophenecarboxylic acid (Compound 22)

To a solution of 0.73 g (1.79 mmol) of methyl 2-[4-methyl-4-(3,5,5,8,8-pentamethyl-5,6,7,8-tetrahydronaphthalene)-2-yl-1E,3E-butadiene-1-yl]-3-thiophenecarboxylate (Compound 21) in 36 ml of tetrahydrofuran was added 9 ml (9 mmol) of 1.0M LiOH solution. The solution was allowed to stir in the dark at room temperature for 1 week. The solution was concentrated in vacuo, diluted with water and stirred with a small amount of hexane. The layers were separated. The aqueous phases was partitioned with 200 ml of ethyl ether, acidified to pH<1 with 1N H₂SO₄ solution and diluted with brine. The organic phase was dried over Na₂SO₄ and concentrated in vacuo to a yellow foam. Purification by flash chromatography (silica gel, 10% ethyl acetate in hexane) followed by recrystallization from boiling acetonitrile yielded the title compound as a yellow crystalline solid.

PMR (d₆ DMSO-): d 1.27 (6H, s) , 1.28 (6H, s), 1.68 (4H, s), 2.19 (3H, s), 2.26 (3H, s), 6.20 (1H, d, J=11.4 Hz), 7.04 (1H, s), 7.07 (1H, d, J=5.5 Hz), 7.08 (1H, s), 7.16 (1H, dd, J=11.4, 15.4 Hz), 7.45 (1H, d, J=5.3 Hz), 7.61 (1H, d, J=15.4 Hz).

2-[4-Methyl-4-(3,5,5,8,8-pentamethyl-5,6,7,8-tetrahydronaphthalene)-2-yl-1Z,3E-butadiene-1-yl]-3-thiophenecarboxylic acid (Compound 23)

Using the same procedure as for the preparation of 2-[4-methyl-4-(3,5,5,8,8-pentamethyl-5,6,7,8-tetrahydronaphthalene)-2-yl-1E,3E-butadiene-1-yl]-3-thiophenecarboxylic acid (Compound 22), but instead using 0.37 g (0.90 mmol) of methyl 2-[4-methyl-4-(3,5,5,8,8-pentamethyl-5,6,7,8-tetrahydronaphthalene)-2-yl-1Z,3E-butadiene-1-yl]-3-thiophenecarboxylate (Compound 20) 4.5 ml (4.5 mmol) of 1.0M LiOH solution and 18 ml of THF after work up (pH=2) gave the title compound as a yellow solid.

PMR (d₆ DMSO-): d 1.23 (6H, s), 1.24 (6H, s), 1.62 (4H, s), 2.14 (3H, s), 2.23 (3H, s), 6.63 (1H, d, J=11.9 Hz ), 6.73 (1H, dd, J=11.5, 11.9 Hz), 7.07 (1H, s), 7.14 (1H, s), 7.38 (1H, d, J=5.4 Hz), 7.43 (1H, d, J=11.5 Hz), 7.51 (1H, d, J=5.4 Hz).

Methyl 2-[4-methyl-4-(3,5,5,8,8-pentametyl-5,6,7,8-tetrahydronaphthalene)-2-yl-1E,3E-butadien-1-yl]benzoate (Compound 24)

Using the same procedures as for the preparation of methyl 2-[4-methyl-4-(3,5,5,8,8-pentamethyl-5,6,7,8-tetrahydronaphthalene)-2-yl-1E,3E-butadien-1-yl]furan-3-carboxylate (Compound 1), but instead using 0.750 g (1.25 mmol) of [(5,6,7,8-tetrahydro-3,5,5,8,8-pentamethylnaphthalene-2-yl)but-3-ene-1-yl] triphenylphosphonium bromide (Compound 32) and 0.207 g (1.26 mmol) of 2-carbomethoxy benzaldehyde (Compound 43) suspended in 3.5 ml of 1,2-epoxybutane, gave the title compound as a clear pale yellow oil.

PMR (CDCl₃); δ 1.28 (12H, s), 1.68 (4H, s), 2.17 (3H, s), 2.27 (3H, s), 3.89 (3H, s), 6.23 (1H, d, J=11 Hz), 7.08 (1H, s), 7.07 (1H, dd, J=11.1 (16 Hz), 7.10 (1H, s), 7.29 (1H, dd, J=1.6, 7.8 Hz), 7.37 (1H, d, J=16 Hz), 7.46–7.51 (1H, m), 7.72 (1H, d, J=7.8 Hz), 7.87 (1H, dd, J=1.6, 7.8 Hz).

What is claimed is:

1. A compound of the formula

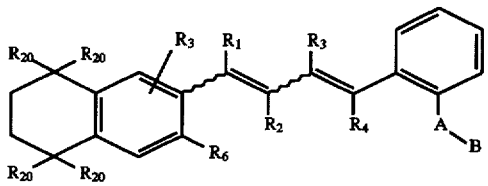

wherein $R_1$–$R_4$ independently are hydrogen, lower alkyl of 1 to 6 carbons, Cl, Br, or I;

$R_5$ is hydrogen, lower alkyl of 1 to 6 carbons, Cl, Br, I, lower alkoxy or lower thioalkoxy of 1–6 carbons;

$R_6$ is hydrogen, lower alkyl, Cl, Br, I, $OR_{11}$, $SR_{11}$, $OCOR_{11}$, $SCOR_{11}$, NH2, $NHR_{11}$, $N(R_{11})_2$, $NHCOR_{11}$ OR $NR_{11}$—$COR_{11}$;

$R_{20}$ is independently hydrogen or lower alkyl;

A is $(CH_2)_n$ where n is 0–5;

B is COOH or a pharmaceutically acceptable salt thereof, $COOR_8$, $CONR_9R_{10}$, —$CH_2OH$, $CH_2OCOR_{11}$, where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1to 10 carbons, or a cycloalkyl group of 5–10 carbons, or phenyl or lower alkylphenyl, $R_{11}$ is lower alkyl, phenyl or lower alkylphenyl.

2. A compound in accordance with claim 1 wherein the A—B group is $(CH_2)_n$—COOH, $(CH_2)_n$—$COOR_8$ or $(CH_2)_n$—$CONR_9R_{10}$, and n is 0, $R_1$ through $R_4$ and $R_6$ are H or methyl, $R_5$ is H, and $R_{20}$ is methyl.

3. A compound in accordance with claim 2 which is selected from the group consisting of methyl 2-[4-methyl-4-(3,5,5,8,8-pentamethyl-5,6,7,8-tetrahydronaphthalene)-2-yl-1E,3E-butadien-1-yl]-benzoate, ethyl 2-[4-methyl-4-(3,5,5,8,8-pentamethyl-5,6,7,8-tetrahydronaphthalene)-2-yl-1E,3E-butadien-1-yl]benzoate, ethyl 2-[4-methyl-4-(3,5,5,8,8-pentamethyl-5,6,7,8-tetrahydronaphthalene)-2-yl-1E,3Z-butadien-1-yl]benzoate, methyl 2-[4-methyl-4-(5,5,8,8-tetramethyl-5,6,7,8-tetrahydro-naphthalene)-2-yl-1E,3Z-butadien-1-yl]benzoate, methyl 2-[4-methyl-4-(5,5,8,8-tetramethyl-5,6,7,8-tetrahydronaphthalene)-2-yl-1E,3E-butadien-1-yl]benzoate, 2-[4-methyl-4-(3,5,5,8,8-pentamethyl-5,6,7,8-tetrahydronaphthalene)-2-yl-1E,3E-butadien-1-yl]benzoic acid and 2-[4-methyl-4-(3,5,5,8,8-pentamethyl-5,6,7,8-tetrahydronaphthalene)-2-yl-1E,3Z-butadien-1-yl]benzoic acid.

4. A method of treating a disease or condition of a mammal which is susceptible to treatment by a retinoid-like compound, with a pharmaceutical composition containing an effective amount of a compound in accordance with claim 1 said disease or condition being selected from dermatoses, Darier's disease, psoriasis, icthyosis, eczema, atopic dermatitis, malignant hyperproliferative diseases, atherosclerosis and restenosis resulting from neointiural hyperproliferation, endometrial hyperplasia, benign prostatic hypertrophy, proliferative vitreal retirropathy and dysplasias, autoimmune diseases, immunological disorders, chronic inflammatory diseases, diseases associated with lipid metabolism and transport such as dyslipidemias, wound healing, dry eye syndrome and sun damage to skin.

* * * * *

UNITED STATES PATENT AND TRADEMARK OFFICE
CERTIFICATE OF CORRECTION

PATENT NO.   : 5,696,162
DATED        : December 9, 1997
INVENTOR(S)  : Chandraratna It is certified that error appears in the above-indentified patent and that said Letters Patent is hereby corrected as shown below:

Title page, item 54, "COMPOUND" should be --COMPOUNDS--.

Column 1, line 3, "COMPOUND" should be --COMPOUNDS--.

Column 1, line 67, "4,810,864" should be --4,810,804--.

Column 3, line 10, "ache" should be -- acne--.

Column 23, line 14, after "butadiene-1", add -- - --.

Column 24, line 59, "0,750" should be --0.750--.

Column 25, line 32, "1tp" should be --1 to--.

UNITED STATES PATENT AND TRADEMARK OFFICE
CERTIFICATE OF CORRECTION

PATENT NO. : 5,696,162
DATED : December 9, 1997
INVENTOR(S) : Chandraratna

It is certified that error appears in the above-indentified patent and that said Letters Patent is hereby corrected as shown below:

Column 1, line 64, "substitutent" should be --substituent--.
Column 2, line 25, "acitivity" should be --activity--.
Column 3, line 11, "icthyosis" should be --ichthyosis--.
Column 3, line 19, "retirropathy" should be --retinopathy--.
Column 3, line 26, "damge" should be --damage--.
Column 4, line 12, after "1", add --)--.
Column 6, line 49, "substitutent" should be --substituent--.
Column 9, line 37, "tetrahydronapthalene" should be "tetrahydronaphthalene--.
Column 9, line 39, "substitutents" should be --substituents--.
Column 9, line 58, after the first occurrence of "and", delete "and".
Column 12, line 8, "dimethlaminopyridine" should be --dimethylaminopyridine--.
Column 12, line 29, "carboetoxy" should be --carboethoxy--.
Column 12, line 48, "(MgSO4)" should be --(MgSO$_4$)--.
Column 12, line 62, "(MgSO4)" should be --(MgSO$_4$)--.
Column 13, line 6, "147" should be --1.47--.
Column 13, line 14, "tetrahydrodnapthalen" should be --tetrahydronaphthalen--.
Column 13, line 17, "trifluroacetate" should be --trifluoro-acetate--.

UNITED STATES PATENT AND TRADEMARK OFFICE
CERTIFICATE OF CORRECTION

PATENT NO. : 5,696,162
DATED : December 9, 1997
INVENTOR(S) : Chandraratna

It is certified that error appears in the above-indentified patent and that said Letters Patent is hereby corrected as shown below:

Column 13, line 48, "tetrahydronapthalen" should be --tetrahydronaphthalen--.
Column 13, line 52, "tetrahydronapthalen" should be --tetrahydronaphthalen--.
Column 13, line 62, "(MgSO4)" should be --(MgSO$_4$)--.
Column 14, line 10, "tetrahydronapthalen" should be --tetrahydronaphthalen--.
Column 14, line 14, "chormatography" should be --chromatography--.
Column 15, line 11, "choride" should be --chloride--.
Column 15, line 27, "tetrahydtronapthalen" should be --tetrahydronaphthalen--.
Column 15, line 62, after "7.56 (1H, d,", add --J=--.
Column 16, line 4, "transfered" should be --transferred--.
Column 16, line 21, after "(1H, d,", add --J=--.
Column 16, line 55, "NaSO$_4$" should be --Na$_2$SO$_4$--.
Column 17, line 7, after "7.37 (1H, d,", add --J=--.
Column 17, line 7, after "7.64 (1H, d,", add --J=--.
Column 17, line 24, after "7.59 (1H, d,", add --J=--.
Column 17, line 38, "partioned" should be --partitioned--.
Column 17, line 41, "thiosufate" should be --thiosulfate--.
Column 17, line 41, "cloride" should be --chloride--.

UNITED STATES PATENT AND TRADEMARK OFFICE
CERTIFICATE OF CORRECTION

PATENT NO. : 5,696,162
DATED : December 9, 1997
INVENTOR(S) : Chandraratna

It is certified that error appears in the above-indentified patent and that said Letters Patent is hereby corrected as shown below:

Column 17, line 45, "colorles" should be --colorless--.
Column 17, line 64, "untill" should be --until--.
Column 18, line 2, "colorles" should be --colorless--.
Column 18, line 5, after "1H, dd, J=3.0, 1.2", add --Hz--.
Column 18, line 12, "transfered" should be --transferred--.
Column 18, line 19, after "solution", delete "and".
Column 18, line 21, "partitoned" should be --partitioned--.
Column 18, line 40, "ethtyl" should be --ethyl--.
Column 18, line 54, after "6.72", delete ",", and add --(--.
Column 19, line 2, after "7.16 (1H, d,", add --J=--.
Column 19, line 23, after "d,", delete ",".
Column 19, line 29, after "Using the", add --same--.
Column 19, line 54, after "6.96(1H, dd,", add --J=--.
Column 20, line 2, after "J=10.2", add --Hz--.
Column 20, line 65, after "(Compound 10", add --)--.
Column 23, line 28, "Parisil" should be --Partisil--.
Column 24, line 19, "was" should be --were--.
Column 24, line 52, "pentametyl" should be --pentamethyl--.
Column 25, line 1, after "J=11.1", delete "(" and add --,--.
Column 25, line 24, "OR" should be --or--.

Signed and Sealed this

Second Day of June, 1998

Attest:

BRUCE LEHMAN

Attesting Officer

Commissioner of Patents and Trademarks